(12) United States Patent
Jimenez et al.

(10) Patent No.: US 8,689,792 B2
(45) Date of Patent: Apr. 8, 2014

(54) OCCLUSION DEVICE AND SYSTEM FOR OCCLUDING A REPRODUCTIVE BODY LUMEN

(75) Inventors: Jose' W. Jimenez, Apple Valley, MN (US); James R. Mujwid, Crystal, MN (US); William S. Tremulis, Minnetrista, MN (US); John R. Frigstad, St. Anthony, MN (US); Karl A. Jagger, Deephaven, MN (US); Kevin R. Arnal, Excelsior, MN (US); Jeffrey P. Callister, Deephavenl, MN (US)

(73) Assignee: Bayer Essure Inc., Milpitas, CA (US)

( * ) Notice: Subject to any disclaimer, the term of this patent is extended or adjusted under 35 U.S.C. 154(b) by 543 days.

(21) Appl. No.: 12/991,907

(22) PCT Filed: May 18, 2009

(86) PCT No.: PCT/US2009/044381
§ 371 (c)(1),
(2), (4) Date: Jan. 14, 2011

(87) PCT Pub. No.: WO2009/140686
PCT Pub. Date: Nov. 19, 2009

(65) Prior Publication Data
US 2011/0130776 A1  Jun. 2, 2011

Related U.S. Application Data

(60) Provisional application No. 61/054,023, filed on May 16, 2008, provisional application No. 61/054,206, filed on May 19, 2008, provisional application No. 61/055,046, filed on May 21, 2008, provisional application No. 61/055,072, filed on May 21, 2008.

(51) Int. Cl.
*A61B 17/08* (2006.01)

(52) U.S. Cl.
USPC ............................................ 128/830; 606/157

(58) Field of Classification Search
USPC .......................... 606/139, 157, 191, 193, 119;
128/830–843; 600/104, 114, 131;
604/117, 208, 515
See application file for complete search history.

(56) References Cited

U.S. PATENT DOCUMENTS 4,785,804 A  *  11/1988   Tlapek et al. .................. 128/841
4,795,438 A  *   1/1989   Kensey et al. .................. 604/22

(Continued)

FOREIGN PATENT DOCUMENTS

WO     WO 2004/100814 A1    11/2004
WO     WO 2005/006991 A      1/2005

(Continued)

OTHER PUBLICATIONS

PCT International Search Report and Written Opinion for International Application No. PCT/US2009/044381 mailed May 12, 2005, 17 pages.

(Continued)

*Primary Examiner* — Julian W Woo
*Assistant Examiner* — Shaun L David
(74) *Attorney, Agent, or Firm* — Blakely, Sokoloff, Taylor & Zafman LLP

(57) ABSTRACT

A system and method of occluding a reproductive body lumen (34) to prevent the passage of reproductive cells through body lumen is disclosed. The system can include a catheter delivery system (10) having a handle device (18), a catheter (10) operatively coupled with the handle device (20), and an occluding device adapted for deployment within the body lumen. The handle device can include a damper device adapted to reduce the vibration on the handle device from deployment of the occluding device from the catheter. Further, the handle device can include an indexing member operatively coupled with the catheter to provide indexing of the catheter.

18 Claims, 24 Drawing Sheets

(56) References Cited

U.S. PATENT DOCUMENTS

| | | | |
|---|---|---|---|
| 6,086,559 A * | 7/2000 | Enk | 604/121 |
| 6,096,052 A * | 8/2000 | Callister et al. | 606/157 |
| 6,432,116 B1 | 8/2002 | Callister | |
| 6,709,667 B1 | 3/2004 | Lowe et al. | |
| 6,763,833 B1 | 7/2004 | Khera et al. | |
| 7,073,504 B2 | 7/2006 | Callister et al. | |
| 2001/0041900 A1 | 11/2001 | Callister et al. | |
| 2005/0045183 A1 * | 3/2005 | Callister et al. | 128/831 |
| 2005/0085844 A1 | 4/2005 | Tremulis et al. | |
| 2005/0192616 A1 | 9/2005 | Callister et al. | |
| 2005/0209633 A1 | 9/2005 | Callister et al. | |
| 2005/0288551 A1 | 12/2005 | Callister et al. | |
| 2006/0009798 A1 | 1/2006 | Callister et al. | |
| 2006/0240063 A9 | 10/2006 | Hunter et al. | |
| 2007/0261699 A1 | 11/2007 | Callister et al. | |
| 2008/0135054 A1 | 6/2008 | Callister et al. | |
| 2008/0275471 A1 * | 11/2008 | Viola | 606/142 |
| 2008/0308110 A1 | 12/2008 | Callister et al. | |

FOREIGN PATENT DOCUMENTS

| | | |
|---|---|---|
| WO | WO 2006/058745 A1 | 6/2006 |
| WO | WO 2008/064280 A | 5/2008 |

OTHER PUBLICATIONS

PCT International Preliminary Report on Patentability for International Application No. PCT/US2009/044381 issued Nov. 17, 2010, 8 pages.

Extended European Search Report for Application No. EP 11184031.0 dated Nov. 21, 2012, 6 pages.

* cited by examiner

OCCLUSION DEVICE AND SYSTEM FOR OCCLUDING A REPRODUCTIVE BODY LUMEN

CROSS-REFERENCE TO RELATED APPLICATIONS

This patent application is a U.S. National Phase application under 35 U.S.C. §371 of International Application No. PCT/US2009/044381, filed on May 18, 2009, entitled OCCLUSION DEVICE AND SYSTEM FOR OCCLUDING A REPRODUCTIVE BODY LUMEN, which claims priority to and the benefit of U.S. Provisional Application No. 61/055,046 filed May 21, 2008, U.S. Provisional Application No. 61/054,023 filed May 16, 2008, U.S. Provisional Application No. 61/055,065 filed May 21, 2008, U.S. Provisional Application No. 61/055,072 filed May 21, 2008, and U.S. Provisional Application No. 61/054,206 filed May 19, 2008; each of said provisional applications incorporated herein by reference in its entirely.

FIELD OF THE INVENTION

This invention generally relates to the field of occluding devices, delivery systems for such devices and the method of using such devices and systems in the occlusion of body lumens or passageways. The invention is particularly useful for the occluding reproductive lumens such as a female patient's fallopian tubes or a male patient's vas deferens to affect contraception.

BACKGROUND OF THE INVENTION

One form of contraception involves the occlusion of reproductive tracts, particularly, the Fallopian tubes in female subjects and the vas deferens in male subjects, with an embolic material and/or occluding device that acutely and/or chronically (following foreign body tissue reaction or epithelialization) blocks passage of sperm through the reproductive tract. Particular forms of occluding devices and systems and methods of inserting the occluding devices in the vas deferens or Fallopian tubes are described in commonly owned U.S. Pat. Nos. 6,096,052 and 6,432,116 and in commonly assigned U.S. Patent Application Publication Nos. 2001/0041900, 2005/0045183, 2005/0085844, 2005/0192616, 2005/0209633, and 2006/0009798, for example, certain features of which are embodied in the Ovion™ permanent contraceptive system sold by the assignee of the present invention. Further occluding devices and systems and methods for disclosing the occluding devices in Fallopian tubes are disclosed in U.S. Pat. Nos. 6,763,833 and 6,709,667, for example.

The transvaginal and transcervical advance of the occluding device delivery catheter to dispose the occluding device in a selected Fallopian tube is aided through the use of an endoscope or hysteroscope that illuminates and provides visualization of the uterine cavity and the ostia of the Fallopian tubes. A flexible hysteroscope is disclosed in commonly assigned US Patent Application Publication No. 2005/0288551 that is employed to guide an occluding device installation catheter through the uterine cavity and into selected ostium of a selected Fallopian tube under such visualization.

It would be desirable to provide contraceptive occlusion systems that provide improved delivery systems, implant structures and configurations.

SUMMARY OF THE INVENTION

The present invention is directed to a contraceptive or sterilization system for occluding a reproductive tract or lumen to prevent the passage of reproductive cells through the tract or lumen. The invention includes an occluding member expandable within the body lumen from a first configuration suitable for introduction into the body lumen to a second larger configuration to facilitate securing the expanded occluding member to at least a portion of a wall which defines the reproductive body lumen. The occluding component of the device may be balloon expandable, self-expandable from the first configuration to the second configuration to occlude the body lumen, or otherwise expandable through actuation of one or more components of a device delivery system.

Various embodiments of the occluding device or member will include structures and materials to promote occlusion, such as denuding features, gels, frames, and the like.

Certain embodiments of the catheter delivery system will include a handle device having one or more dampening or damper devices. These dampening devices are configured to reduce handle "jumping" or vibration that often occurs during deployment of occluding members in conventional systems. Exemplary embodiments of the damper devices may include a pneumatic damper device, a centrifugal brake damper device, a press-in elastomer damper device, and a compression point damper device.

Various embodiments of the handle device for use with a catheter delivery system may also include a hysterscope deployment support device. The support device selectively attaches to the handle and is capable of sliding forward and rearward along a portion of the handle, and twisting or rotating around the handle. This structural connection between the support and handle devices frees up the hands of the physician during a procedure because he or she is not required to separately secure, grab or manipulate each of the devices separately.

Embodiments of the catheter delivery system can include a catheter tip portion configured to denude or disrupt the tissue within the body lumen to further promote tissue in-growth within and occlusion by the occluding member.

To promote and facilitate occlusion of the body lumen, a TUDD device can be employed with the catheter delivery system of the present invention. The TUDD device sprays or injects a scarring agent into the body lumen to promote occlusion.

Various contraceptive occlusion devices and delivery systems disclosed in U.S. Patent Application Publication Nos., 2005/0045183, 2005/0209633 and 2008/0308110 can be employed, in whole or in part, with the present invention. As a result, each of the above-identified disclosures and publications is incorporated herein by reference in its entirety.

Figure 1:
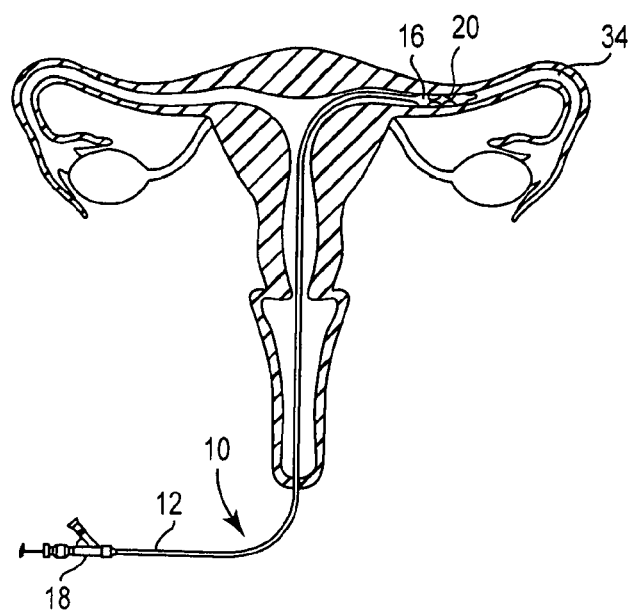
FIG. 1 is an illustration in partial cross-section depicting the transvaginal and transcervical advancement of a catheter delivery system and occluding device in a female patient's Fallopian tube.

It will be understood that the drawing figures are not necessarily to scale.

DETAILED DESCRIPTION OF PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for occlusion of reproductive body lumens to affect contraception.

It will be understood that the term "contraceptive device," "occlude," "occluding device," "implant," "occluding implant" or "occluding member" encompass any type of a device adapted to be delivered into and released or otherwise disposed in a reproductive tract or lumen to acutely and/or chronically occlude the reproductive tract lumen.

Figure 2:
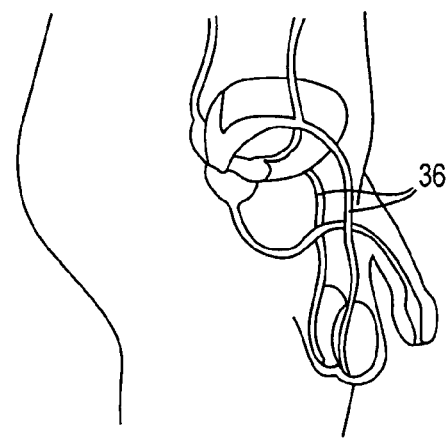
FIG. 2 is an illustration in partial cross-section depicting the vas deferens of a male patient.
Figure 3:
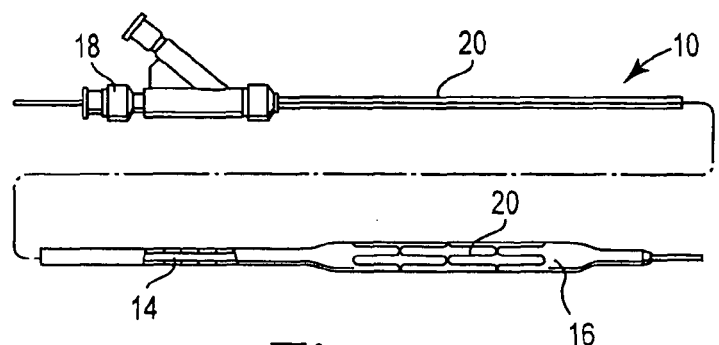
FIG. 3 is a side view of an exemplary catheter delivery system.

Referring generally to FIGS. 1-3, an embodiment is shown of a catheter delivery system 10 available in the practice of the invention, which comprises an elongated shaft 12 having a lumen which is in communication with a member 16 mounted on a distal section of the catheter shaft 12. An occluding member or implant device 20, such as a self-supporting member, can closely conform to the diameter of the member 16 to facilitate introduction into the desired body lumen. Occluding member 20 can also be disposed at the distal shaft 12 without the employment of member 16. Occluding member 20 can be formed so that it has a collapsed configuration (e.g., with shape memory) with relatively small transverse dimensions. The occluding member 20 may be deformed to facilitate mounting or disposal onto or into the member 16, or directly onto the shaft 12, and is expandable to an open expanded configuration within a body lumen. In certain embodiments, the occluding member 20 can include an open, lattice-type structure facilitating endothelialization which secures the occluding member to the wall defining the body lumen. Occluding member 20 can be deformed to an expanded diameter, preferably equal to or slightly larger than the dimensions of the body lumen within which the occluding member is to be disposed. For disposition within a female patient's fallopian tubes, the expanded transverse dimensions can be approximately 0.1 mm to about 5 mm.

The occluding member 20 may have a number of suitable configurations as shown schematically in FIGS. 5-11. Occluding member 20 may be constructed from a length of shape-memory hypodermic tubing. Nitinol, shape-memory wire, slotted plastic or metal tubing, braided tubing or material, and can take on or resemble the shape of a ribbon, ring, coil, spring, and a myriad of other shapes and designs.

The practice of the invention can comprise the following general steps. The occluding member 20 having relatively small transverse dimension is mounted onto the exterior of the catheter 10 shaft 12, or at a member 16 at a distal end of the shaft 12. The shaft 12 may include a lumen along a portion thereof for introduction and selective containment of the occluding member 20. The catheter 10 can be advanced under fluoroscopic or endoscopic visualization until occluding member 20 is positioned within one of the female patient's fallopian tubes 34, as shown in FIG. 1. In those embodiments utilizing a ballooning device, Inflation fluid is introduced to inflate an inflatable member 16. Inflation of member 16 expands occluding member 20 to an open configuration, lodging it in body lumen 34. Catheter 10 is removed, leaving the expanded occluding member 20 implanted in body lumen 34. Another expandable member is delivered to the patient's other fallopian tube and expanded therein in the same manner. Alternatively, the occluding member may be expanded into or positioned within the vas deferens 36 of a male patient, as shown in FIG. 2, to provide male contraception using the same or similar procedures.

Figure 4:
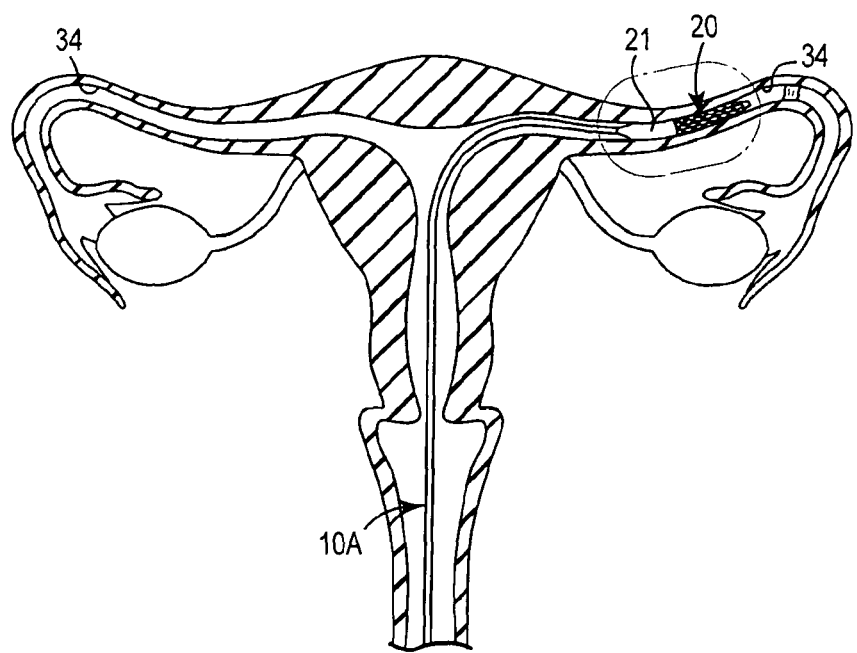
FIG. 4 is an illustration in partial cross-section depicting the transvaginal and transcervical advancement of a catheter delivery system, TUDD device, and occluding device in a female patient's Fallopian tube.
Figure 5:
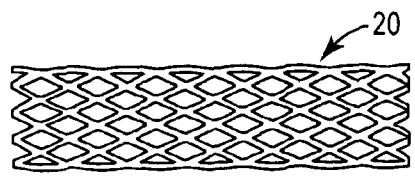
FIGS. 5-11 show various exemplary occluding devices capable of use with the present invention.
Figure 6:
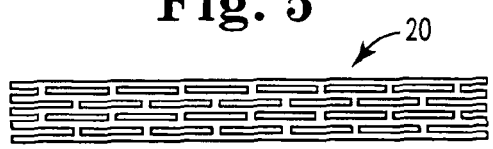
Figure 7:
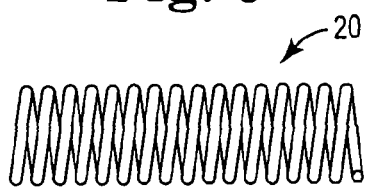
Figure 8:
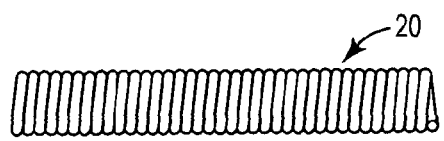
Figure 9:
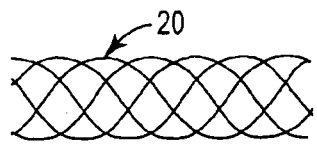
Figure 10:
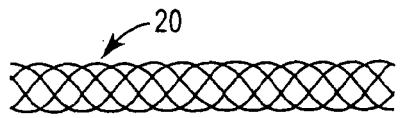
Figure 11:
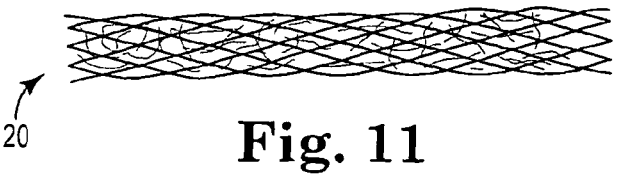

The catheter delivery system 10A of FIG. 4 further includes a TUDD device 21 provided proximate the occluding member 20. The TUDD device 21 can locally inject or spray a scarring agent before and/or after insertion or deployment of the occluding member 20 to promote scarring within the body lumen 34, on either side of the member 20. Scarring will, in turn, promote and speed up the tissue in-growth process and occlusion. In alternate embodiments, the TUDD device 21 can be provided with the system 10A without an occluding member 20. With such an embodiment, the TUDD device 21 can inject or spray the scarring agent at a plurality of places along the body lumen 34 to promote scarring and occlusion within the lumen 34. The occlusion would then be reversible as the scar tissue could be pierced or otherwise removed or compromised to re-open the body lumen 34. Various devices, systems and methods disclosed in U.S. Pat. Nos. 7,073,504, 6,432,116 and 6,096,052, as well as U.S. Published Application No. 2006/0240063 can be employed with the present invention and are, therefore, incorporated herein by reference in their entirety.

Embodiments of the present invention may use various methods and systems for expanding the occluding member 20 within the body lumen 34. For instance, in one embodiment, the occluding member 20 may be forced out of or released from the shaft or member 16, or the shaft 12 or member 16 may be released or pulled back from occluding device 20 while within the body lumen such that the occluding device 20 is permitted to expand or otherwise deploy under its own construction or shape memory configuration to contact and become disposed within the body lumen. Upon deployment and positioning, endothelial tissue that forms within or around the structure of the occluding member 20 helps block and seal the lumen so as to prevent the passage of reproductive cells, eggs or sperm cells. The occluding member 20 may include denuding surfaces, structures or features adapted to facilitate tissue disruption or trauma to promote endothelialization. Other known catheter delivery systems, and occluding systems and members, can be employed with the present invention, including those disclosed in U.S. Pat. No. 7,073,504, and U.S. Patent Publication Nos. 2005/0045183, 2005/0209633, 2007/0261699, 2008/0135054 and 2008/0308110, each of which is hereby incorporated by reference in its entirety.

As detailed herein, the expansion of the diameter of occluding member 20 is effected either by use of an expanding device, e.g., an inflatable balloon at the delivery catheter distal end disposed within the occluding device lumen 14 or by self-expansion or self-deployment upon release from confinement within a device delivery lumen of the catheter delivery system 10. The tubular member may be fabricated in the fashion of a tubular member or in any of the ways and configurations disclosed in the above-referenced patents and publications. In addition to the potential shapes and configurations for the occluding member 20 described herein, a myriad of known biocompatible materials can be used to construct all or portions of the occluding member 20. The occluding member 20 may take other forms as shown in the various embodiments of occluding devices depicted in the above-cited references or otherwise known in the art. When deployed or expanded, the occluding member 20 may have a substantially uniform transverse dimension along its length or may be tapered along its length. The occluding member 20 may be substantially shorter than as depicted.

In one embodiment, occlusion can be achieved by placement of a gel 50 onto an external surface of the occluding implant 20 that is designed to be placed into a body lumen of a patient. The gel 50 creates a seal with the lumen, e.g., fallopian tube, thereby preventing the passage of reproductive cells. Given the undulating nature of a fallopian tube's inner surface, the gel 50 acts in conjunction with the compressive feature of the implant 20 to fill in any small spaces or gaps between the implant 20 and the inner surface of the fallopian tube, thereby creating an air and fluid tight seal.

The gel 50 may be a hydrogel that is capable of being applied to the surface of the implant 20 so that it remains dry while in the package or kit, but hydrates upon implantation. The fluid within the uterus and the fallopian tube is able to act as the hydrating fluid for the gel 50. In another embodiment, it is possible to have a physician hydrate the gel 50 with another type of fluid, such as saline, prior to or after implantation. It is envisioned that the time, location and durability of the hydrated gel can be controlled through different process steps, including chemistry and grafting to the implant surface. In one embodiment, when un-hydrated, gels 50 are used that can be very thin and capable of being delivered on implants 20 through the use of catheters.

It is possible to have the gel 50 have benign properties such that it does not illicit any tissue reaction and only forms a seal with the inner surface of the fallopian tube. It is also possible to impart into or provide reactive properties with the gel 50 such that it acts as an irritant and causes a tissue reaction and promotes tissue in-growth into the gel 50, the implant 20, or both. Gels 50 that may be used to promote tissue in-growth between the fallopian tube and an implant 20, or alone in the fallopian tube, can include alginate, chitosan, hyaluronan, polyethylene oxide/polypropylene oxide or other gels known to those skilled in the art.

Figure 12:
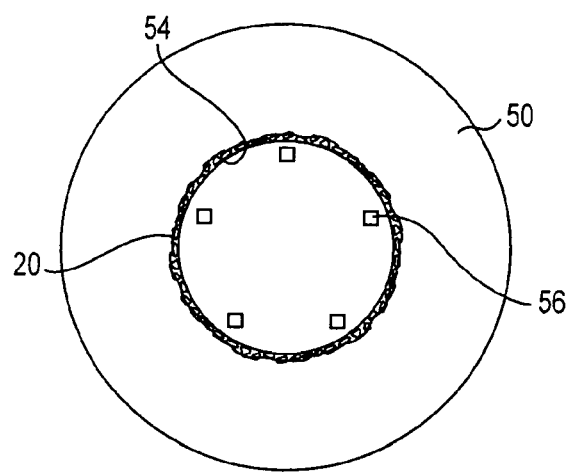
FIG. 12 is front elevation view of an occluding device to be implanted in a patient's Fallopian tube or other body lumen.
Figure 13:
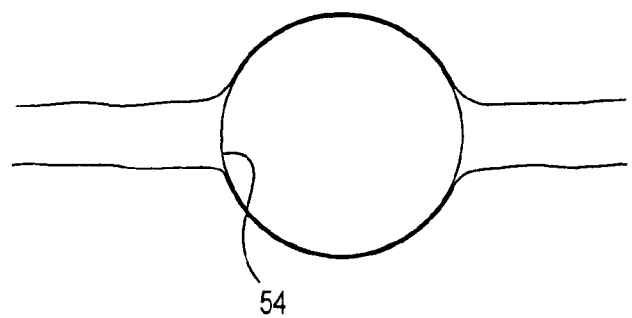
FIG. 13 is a side view of the occluding device in an inflated state in a Fallopian tube or other body lumen.

In another embodiment of the invention, as illustrated in FIGS. 12-13, a balloon 54 can be disposed to an expandable frame 56. The frame 56 can include one or more fibers for in-growth and/or geometrical features to induce trauma on the inner surface of the fallopian tube. The tissue trauma causes a response that allows for tissue in-growth over time, thereby creating a biological occlusion. While the biological occlusion is forming, the balloon 54, upon implantation, can be radially expanded to a diameter 2-4 times that of the fallopian tube inner diameter. The large expansion smoothes out the inner surface of the fallopian tube and creates a tight, compressive seal between the balloon 54 and the fallopian tube 34. In the embodiment illustrated in FIG. 12, it is possible to include a balloon 54 with the gel-covered implant 20 to press the gel 50 into the inner surface of the fallopian tube tissue.

The balloon 54 can be configured to expand independently of the frame 56 to create an immediate occlusion in the fallopian tube. It is also possible to have the balloon 54 and frame 56 expand together. The balloon 54 can be placed either proximally, distally or on both ends of the frame 56. It is also possible to have a number of balloons 54 spaced along a length of the frame 56.

Figure 14:
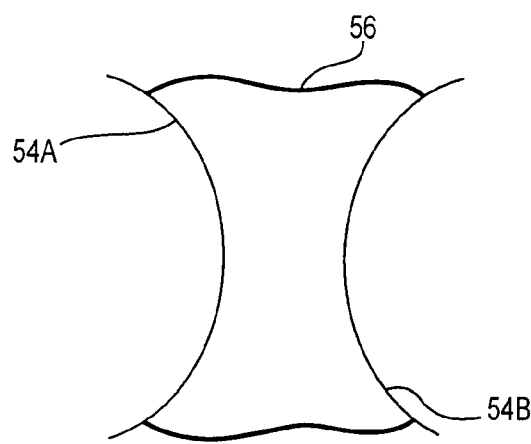
FIG. 14 is a partial view of shell portions of an inflatable occluding device.

The balloon 54 can be filled with any bio-compatible material such as air, saline, hydrogels, methylmethacrylate and other materials known to those skilled in the art to create a range of filled balloon 54 durometers. Further, embodiments of the balloon 54 can be manufactured from one or more shells or portions joined together as shown in FIG. 14. In one embodiment, the balloon 54 comprises a first shell portion 54A and a second shell portion 54B that are attached to an inner diameter of an expandable frame 56. As the frame expands, the first shell portion and the second shell portion of the balloon 54 expand to cerate a dual barrier within the fallopian tube. The expansive force of the frame is such that the contact between the membrane of the balloon 54 and the fallopian tube forms a compressive seal, thus preventing any material transfer. Over time, the components of the frame (e.g., fiber for in-growth and geometrical features to induce trauma on the inner surface of the fallopian tube) allow for tissue in-growth to create a biological occlusion. The balloon 54, or the first shell portion and the second shell portion can be inflated by use of a catheter or any other inflating device known to one skilled in the art.

Figure 15:
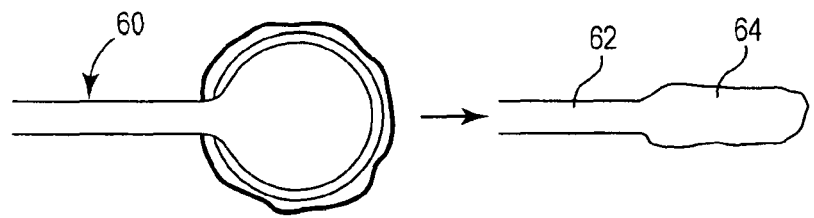
FIG. 15 is side view of an occluding device in an inflated state and a deflated state.
Figure 16:
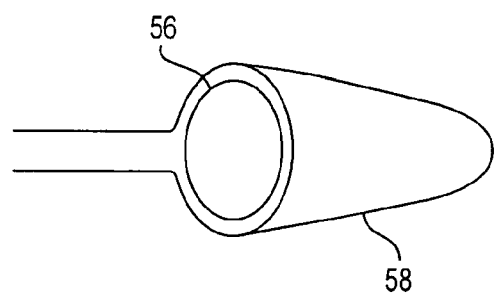
FIG. 16 is a side view of an occluding device in an expanded state with a membrane.

In another embodiment of the invention, as illustrated in FIG. 15, a frame member 60 is provided with an arm portion 62 and a collapsible portion 64. The collapsible portion 64 can be attached or coupled to an expansion member 66 that can be expanded into a generally open circular shape, as illustrated in FIG. 16. A non-porous membrane 68 can be attached or coupled to the expansion member 66. The expansion member 66 can open against the fallopian tube wall while the membrane 68 extends distally into the fallopian tube creating an instant barrier to reproductive cells and other material. The frame member 60 and expansion member can be manufactured from Nitinol. PET and other compatible materials known to one skilled in the art.

Figure 17:
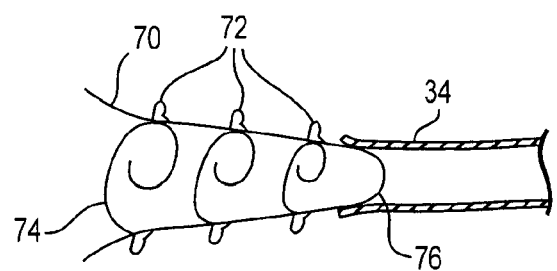
FIG. 17 is a partial cross section view of an expandable occluding device within a body lumen.

As illustrated in FIG. 17, a frame assembly 70 can be provided that expands to form a generally wedge shape once it is inserted or deployed in a patient's body lumen. Arm members 72 can be integral with or disposed on the frame 70 to engage the inner surface of the fallopian tube. The arm members 72 can have any design that is capable of causing a plurality of tissue trauma to the inner surface of the fallopian tube, which will allow a tissue in-growth response to occur. The arm portions 72 design can include, but is not limited to, a single or multiple barb shape, a coil shape, or single or multiple brushes or bristles. Other shapes are also envisioned and therefore the listed shapes or designs should not be considered limiting. It is also possible to have arm portions that are static, or movable from a first position to at least one additional, or second, position. The movement of the arm portions 72 can cause additional tissue trauma and thus increase tissue in-growth.

The expansion of the frame assembly 70 can be controlled by the material properties and/or expansion actuators 74 between the arm portion 72 and the frame assembly 70. The expansion actuators 74 can comprise springs or coiled springs that either unfold, unwind, uncoil, or otherwise expand. The expansion actuators 74 can vary in shape, size and design along a longitudinal axis of the frame assembly 70, as illustrated in the exemplary embodiment of FIG. 17. As particularly illustrated in the embodiment of the FIG. 17, the expansion actuators 74 can be generally smaller or expand less as they are positioned from one end of the frame assembly 70 to the other. This difference in size or expansion permits the device to have a generally wedge or tapered plug shape. One of the advantages of this type of shape is to account for the varying or undulating inner surface of the fallopian tube. Other shapes and configurations are also possible and are to be considered to be within the spirit and scope of the invention.

A membrane 76 can be attached to or disposed to the frame assembly 70 to act as a barrier to reproductive cells. The membrane 76 can be disposed on an exterior or interior surface of the frame assembly 76.

Figure 18:
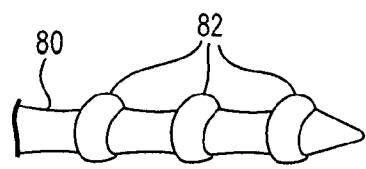
FIG. 18 is a side view of an occluding device.

As illustrated in FIG. 18, the body lumen can be occluded or totally blocked by an insert 80 that can have a generally conical shape and which can include at least one flared portion 82 that extends from an outer surface of the insert 80. The flared portion 82 is designed to engage or abut the inner surface of the fallopian tube and thus prevent passage of any reproductive cells. In the exemplary embodiment of FIG. 18, there are several spaced flared portions that extend generally concentrically away from the outer surface of the insert 80. It is also possible to have flared portions of differing size. For example, the flared portion 82 nearest the vertex can be smaller, with the flared portions 82 generally getting larger further from the vertex.

In one exemplary embodiment, the insert 80, the flared portion 82, or both, can comprise a compressible material such as a polymeric foam or rubber. Other compressible and non-compressible materials can also be employed. One advantage of a compressible material is that it can be reduced in size for placement in a catheter or other delivery device and then self-expanded once it is placed in the body lumen. The expansion of the insert 80 can also assist in causing tissue trauma, and thus tissue in-growth, when the outer surface of the insert 80 is modified in such a way that it engages the tissue. For example, the outer surface of the insert 80 can include barbs, coils and the like. It is also envisioned that the insert 80 can include a generally rough surface capable of causing trauma to the fallopian tube tissue.

Figure 19:
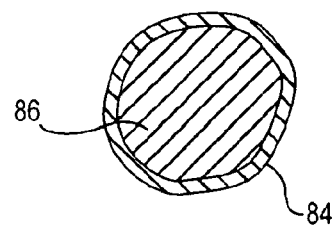
FIG. 19 is a cross section view of an occluding device, illustrating open and closed cell foam portions.

As illustrated in FIG. 19, the insert 80 can include an outer shell 84. The outer shell 84 can comprise a closed-cell foam that encases a core 86 of open-cell foam. In addition, the insert 80 can include a generally porous portion between the flared portion(s) 82 and/or fibers (not shown) that will aid in tissue in-growth.

Figure 20:
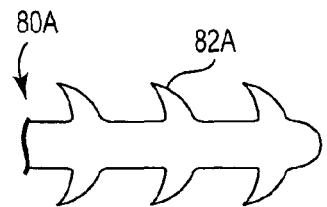
FIG. 20 is a side view of an occluding device.
Figures 21, 21A:
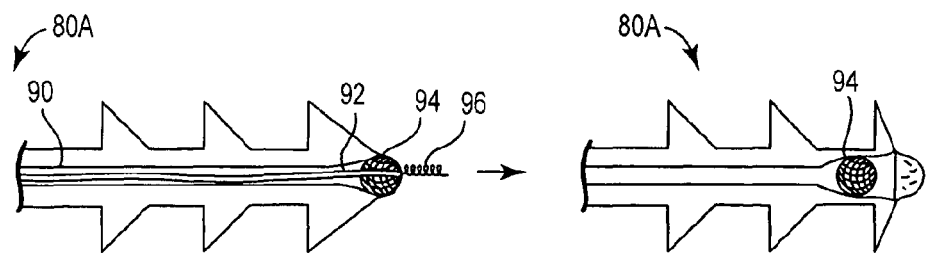
FIG. 21 is a cross section view of the occluding device of FIG. 20 in a natural or implanting state.
FIG. 21A is a cross section view of the occluding device of FIG. 20 in an implanted and expanded state.

As illustrated in FIGS. 20-21A, an insert 80A, which can be generally cylindrical, can include at least one flared portion or surfaces 82A extending along at least a portion of its length, or multiple flared portions or surfaces 82A spaced along at least a portion of its length. The flared portion(s) 82A can take on any shape or design that will facilitate placement of the insert 80A in the fallopian tube of the patient. In addition, a flared portion(s) 82A can be provided that can generate tissue trauma as described above.

In one exemplary embodiment, a lumen 90 can extend generally along a length of the insert 80A. The lumen 90 can have a generally consistent diameter or a varying diameter along its length. A tether 92 can be attached to a retracting member 94 that is at least partially disposed in the lumen 90 and positioned at a leading end of the insert 80A. The tether 92 generally extends through and along a length of the lumen 90 such that a physician can pull on it to retract the retracting member 94 away from the leading end and further into the lumen 90. As the retracting member 94 is retracted it causes an outer diameter of the insert 80A to expand, thus forcing the flared portions 82A to engage an inner surface of the fallopian tube. The flared portions 82A thus act as a plug to block or occlude the passage, thus preventing the movement of reproductive cells and other materials.

In one example embodiment it is possible to have a latch mechanism (not shown) in the lumen 90 that retains the retracting member 94 as it moves away from the leading end and into the lumen 90. The latch mechanism prevents the retracting member 94 from moving back toward the leading end, thereby assisting in preventing the collapse of the insert 80A. The latch mechanism can comprise ridges, tines, barbs or any other like structure extending away from an inner surface of the lumen 90 that is capable of stopping movement of the retracting member 94 back toward the leading end of the insert 80A.

The retracting member 94 can take on any shape such as a sphere, cone, pyramid, and the like that is capable of expanding a circumferential diameter of the insert 80A. The retracting member 94 can also be manufactured from any material that will permit it to more easily move in the lumen 90 and expand the insert 80A.

Extending away from the retracting member 94 in a generally opposite direction of the tether 92 can be a lead tether 96. The tether 96 can include a rounded end that extends away from the leading end of the insert 80A. The lead tether 96 can aid in the positioning, navigation and tracking within the patient's body. The lead tether 96 can also comprise a coil wire, spring, thread or any other material capable of denuding tissue or otherwise functioning as described herein.

Figure 22:
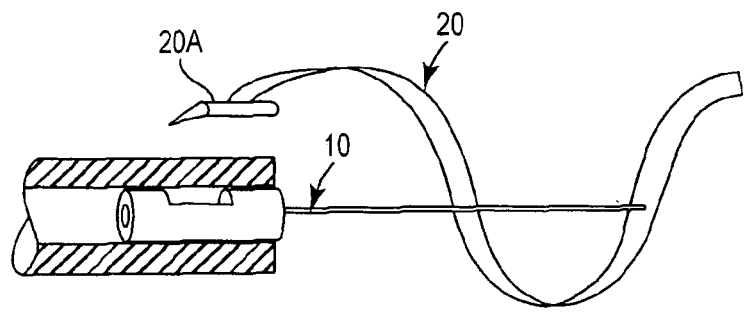
FIG. 22 is partial cross section view of a ribbon occluding device and corresponding catheter connection.

In another embodiment, as shown in FIGS. 22-27, the occluding member or implant 20 can be constructed as a ribbon (e.g., hexagonal ribbon) rather than a coil. Such a ribbon configuration features sharp bends, or angled portions (FIG. 27) to provide advantageous tissue denuding features to abrade the epithelial surfaces of the body lumen 34 during deployment to promote tissue in-growth. As depicted in FIG. 22, the ribbon member 20 can include an attachment member 20A that is shaped and sized to fit into the recess of a portion of the delivery catheter 20, such as the hypo tube, to lock (directly or indirectly) the two parts together. This locking feature assists in preventing the ribbon 20 from unwinding while still within the catheter. Various other configurations and features may be employed to lock or otherwise fit the ribbon and catheter together without deviating from the present invention. The ribbon member 20, in one embodiment, will be approximately 2 mm in cross section, and approximately 25 mm in length.

Figure 23:
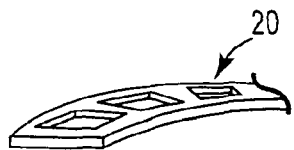
FIG. 23 is a partial view of a portion of a denuding occluding device.
Figure 24:
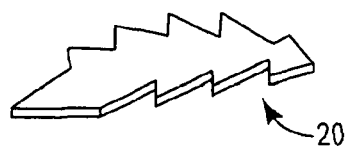
FIG. 24 is a partial view of a portion of a denuding occluding device.
Figure 25:
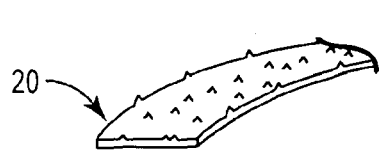
FIG. 25 is a partial view of a portion of a denuding occluding device.
Figure 26:
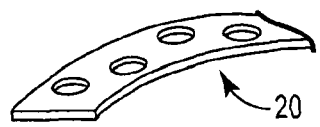
FIG. 26 is a partial view of a portion of a denuding occluding device.
Figure 27:
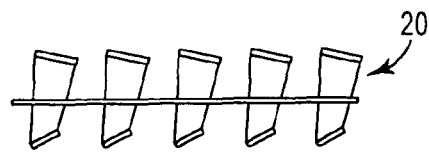
FIG. 27 is a partial cross section view of a ribbon occluding device.

FIGS. 23-26 show various tissue-denuding designs or features that can be included on a portion of the occluding member 20, including ribbon member 20. FIGS. 23 and 25-26 show various surface features provided with the member 20 to facilitate denution. Various apertures and/or rough or textured surface features can be included to denude the wall of the body lumen 34 during deployment. FIG. 24 depicts an embodiment of the occluding member 20 having serrated edges to achieve tissue denution. These denution configurations not only assist in faster occlusion, but in more durable long-term fibrotic response for the occlusion process. It is understood that these denution features can be utilized with any of the occluding members 20 described herein, in addition to the ribbon member 20. The various described and depicted occluding members 20 can be constructed of known biocompatible metal and polymer materials such as Nitinol, PET, and the like. The dimensions and shapes of various occluding members 20 can be adjusted to tailor a specific anatomical fit, reduce spacing for in-growth, and the like.

The occluding member 20 can be at least partially formed of or coated with any of the drugs, materials, features or mechanisms disclosed in U.S. Patent Publication No. 2006/0009798, which is hereby incorporated by reference in its entirety. Such configurations or coatings generally promote epithelialization within body tissues to create a more effective occlusion of the body lumen 34, or result in a more secure attachment of the occluding member 20 to the body lumen wall. For instance, polyester or like fibers may be attached to one or more expandable segments of the occluding member 20 to bear against the body lumen wall such that tissue in-growth occurs more rapidly.

Further, a slow-release contraceptive substance may also be embedded into or with at least a portion of the occluding member 20 to provide contraception during the time that it takes for tissue in-growth to fully obstruct the occluding member 20. Exemplary systems and techniques capable of use with the present invention are disclosed in previously-incorporated U.S. Patent Publication Nos. 2005/0045183 and 2006/0009798.

In various embodiments, a marking member or portion can be disposed or provided along a portion of the occluding member 20 or shaft 12 to facilitate visual positioning or tracking of the occluding member 20 and/or the shaft 12 during the deployment process.

Certain embodiments of the present invention can include a handle device or mechanism 18 as shown in FIG. 1 for use with the catheter delivery system 10 of the present invention. Other embodiments of the handle device are also envisioned for use with the present invention.

Figure 28:
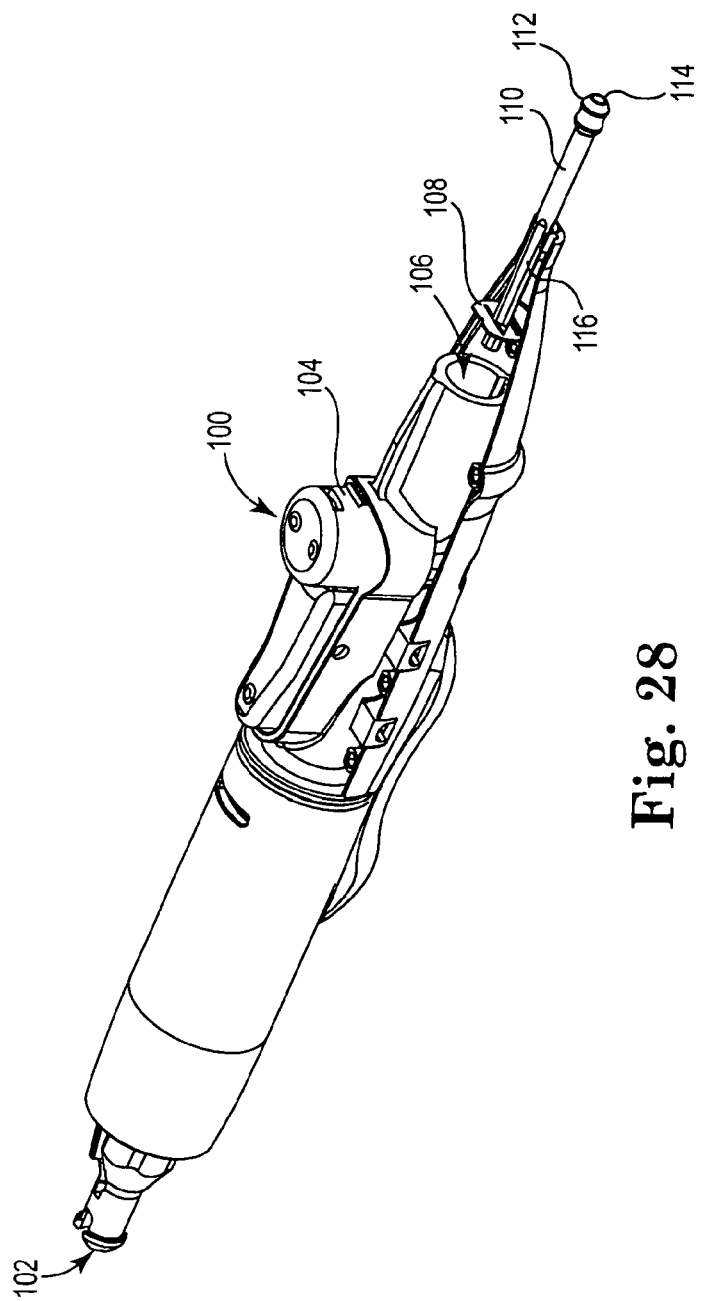
FIG. 28 is a perspective view of an indexing handle device for use with a catheter delivery system of the present invention.

In one embodiment, as shown in FIG. 28, a handle device 100 can be employed at the proximal end of the catheter delivery system 10 to control and facilitate deployment of the occluding device 20. Handle device 100 can be constructed in a clam-shell configuration, wherein the device 100 includes one or more removable covers adapted to provide selective access to the internal components of the device 100. With such a clam-shell configuration or design, the components of the handle 100 can be easily replaced, repaired or otherwise accessed. For example, FIG. 28 shows a portion of the clam-shell handle device 100 removed to expose components at the distal end of the handle. The clam-shell handle 100 can include a proximal interface port 102, an actuator 104, and a lumen 106. Further included with this embodiment is a locking disc 108 and an indexing tube or member 110. The indexing tube 110 can include a sheath interface 112 and one or more anti-torque flats 116. The sheath interface 112 includes a lumen 114 there through and is adapted to operatively connect with a catheter or catheter sheath.

The indexing tube 110 is longitudinally slidable along its plane within the device 100, through the locking disc 108 toward the lumen 106. This, in turn, permits length adjustment and deployment of the catheter sheath attached to the tube 110 at the sheath interface 112. The sheath interface can be colored (e.g., black) to promote visualization, and the tube 110 can be opaque or black. Various colored strip, or location indicator indicia or coding features can be provided along defined lengths of the tube 110 to further promote visualization during use.

Rotational movement of the sheath and tube 110 is generally limited. Namely, the anti-torque flats 116 interface with a corresponding feature in the locking disc 108 to restrict rotation or turning of the tube 110 about the axis of the tube 110. This rotational restriction increases control and indexing capabilities of the catheter and sheath during first and second deployments of the occluding members 20.

Figure 29:
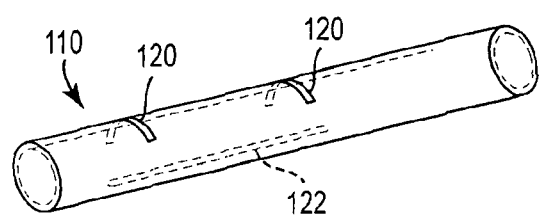
FIG. 29 is a perspective view of an indexing tube for the handle device of FIG. 28.
Figure 30:
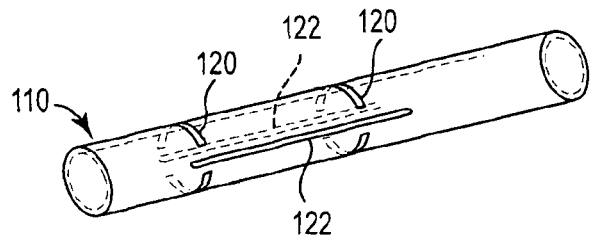
FIG. 30 is a perspective view of an indexing tube for the handle device of FIG. 28.
Figure 31:
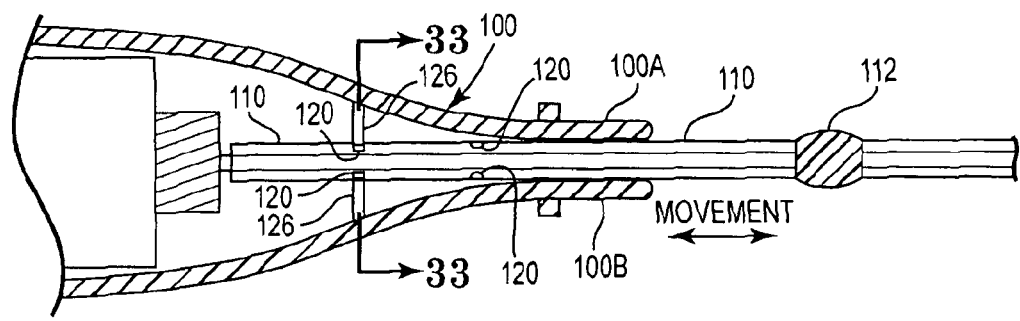
FIG. 31 is a partial cross section view of an indexing handle device for use with a catheter delivery system of the present invention.
Figure 32:
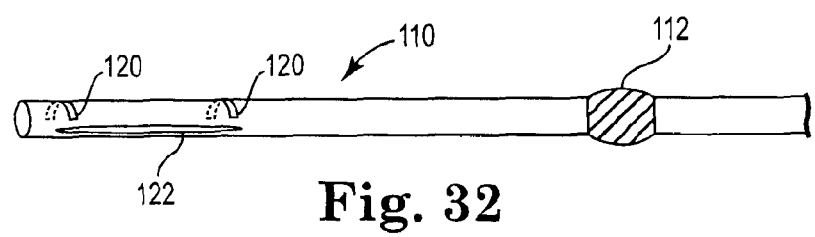
FIG. 32 is a partial view of an indexing tube for the handle of FIG. 31.
Figure 33:
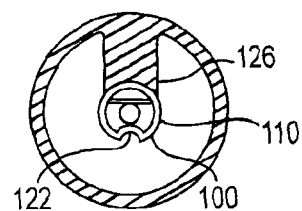
FIG. 33 is a partial cross section view along line 33-33 of FIG. 31.

In another embodiment designed to increase indexing of the catheter and sheath during deployment, as shown in FIGS. 29-33, the indexing tube 110 can include one or more indicator slots 120 and/or indicator grooves 122, as shown in FIGS. 29-30. The indicators 120, 122 interface with engagement portions of the handle 100 to provide predefined longitudinal travel paths. For instance, the travel distance of the tube 110 can be predefined to the length of the indicator grooves 122 with predefined snap stop positions at the indicator slots 120. As such, in one embodiment of the tube 110, the grooves 122 extend along a limited length or portion of the tube 110 and the slots 120 extend around a limited portion of the tube 110. The one or more grooves 122 can mate with an extension portion of the handle 100 to serve as an anti-torque groove to restrict rotation or spinning of the tube 110 during use, as shown in FIG. 33. The one or more grooves 122 can be used alone or in combination with other features (e.g., the flats 116) to control or limit rotation.

As shown in FIGS. 31-33, snap stop members or features 126 are positioned within the handle 100 to extend down into engagement with the longitudinally slidable indexing tube 110 and, namely, the slots 120 of the tube 110. The stop features 126 can be spring loaded, flexible, or generally rigid, and can be constructed of a myriad of materials, such as known polymers and metals. These stop and anti-torque features of the indexing tube 110 enable a physician to better control deployment accuracy during an implant procedure. Further, the sheath interface or grip 112 can be shaped, as best shown in FIG. 28, to define a gripping point (e.g., thumb grip) that also promotes manual manipulation of the tube 110 and the connected catheter sheath. These increased manual manipulation and indexing capabilities of the indexing tube 110 embodiments are particularly important between first and second implant deployments, and when visualization and distention of the uterus makes placement or positioning accuracy difficult during a surgical procedure.

In various other embodiments, as shown in FIGS. 34-43, the handle device 100 is configured and designed to provide better controlled deployment once the deployment button or actuator 104 is pushed or otherwise engaged. Namely, the speed of the deployment is regulated via the handle device 100, and "jumping" of the handle 100 during deployment is substantially reduced. These features provide more accurate placement and smoother deployment during use.

Figure 34:
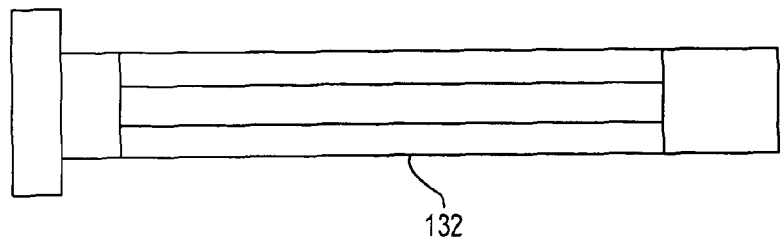
FIG. 34 is a side view of an elongate nut for use with a dampening handle device.
Figure 35:
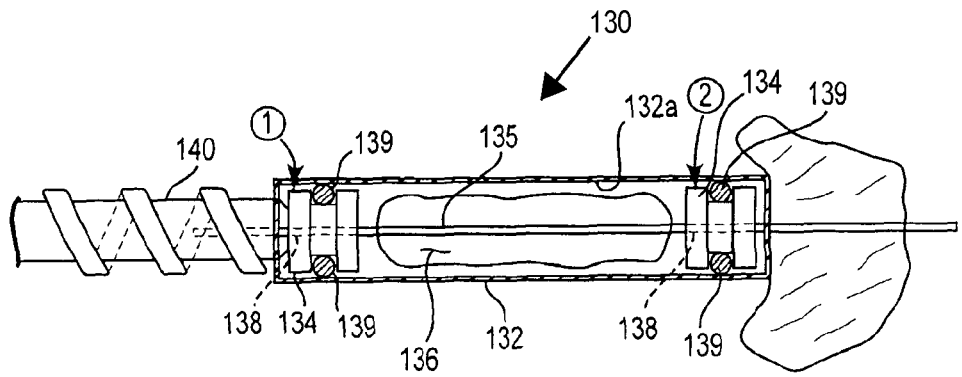
FIG. 35 is a partial cross section view of a pneumatic dampening device for use with a dampening handle device.
Figure 36:
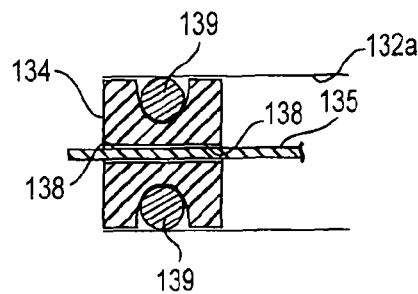
FIG. 36 is a partial cross section view of a plug portion of the pneumatic dampening device of FIG. 35.

In one embodiment, a pneumatic damper system 130 is provided with the handle device 100, as shown in FIGS. 34-36. The damper system 130 can include an elongate nut component 132 connectable to the handle 100 to extend out a distal portion of the handle 100 for operatively interfacing with the catheter system. The nut component 132 generally includes a lumen or bore 132a extending there through, with an inner diameter of approximately 0.148 inches to 0.160 inches. Variations of these dimensions are envisioned for use with the present invention.

The nut 132 can include a plug 134 disposed therein. The plug can be constructed of Delrin™ (polyoxymethylene), or like materials known to one skilled in the art. The plug 134 can include a plug bore 138 in fluid communication with the nut bore 132a. The plug 134 can further include one or more friction o-rings 139 or other sealing features provided around a portion of the plug 134, as depicted in FIGS. 35-36. A driving piston or member 140 is provided for displacement and engagement against the plug 134, as shown in FIG. 35. The piston or member 140 can be threaded or otherwise configured for forward and rearward longitudinal displacement. A stabilizing wire or member 135 can extend through the respective bores 132a, 138 to provide a stabilizing traversal path for the plug 134 within the bore 132a of the elongate nut. Compressed air 136 is present within the bore 132a.

As shown in FIG. 35, the displacement of the piston 140 against the plug 134, generally caused by withdrawal of the catheter during deployment, causes the plug 134 to travel from an initial position 1 to a second position 2 at the back portion of the nut and handle, distal the catheter or sheath attachment. A controlled jet or poring of air through the plug 134 and bore 132a causes the plug 134 to bottom out at the back of the bore 132a which, in turn, creates a pneumatic seal at the base of the handle. Variations in the diameter of the wire 135 and/or the plug bore 138 further control the jet and the pneumatic sealing or dampening affect. The friction of the o-ring 139 around the interior of the bore 132a during displacement provides additional dampening control over the traversal speed of the plug 134.

Figure 37:
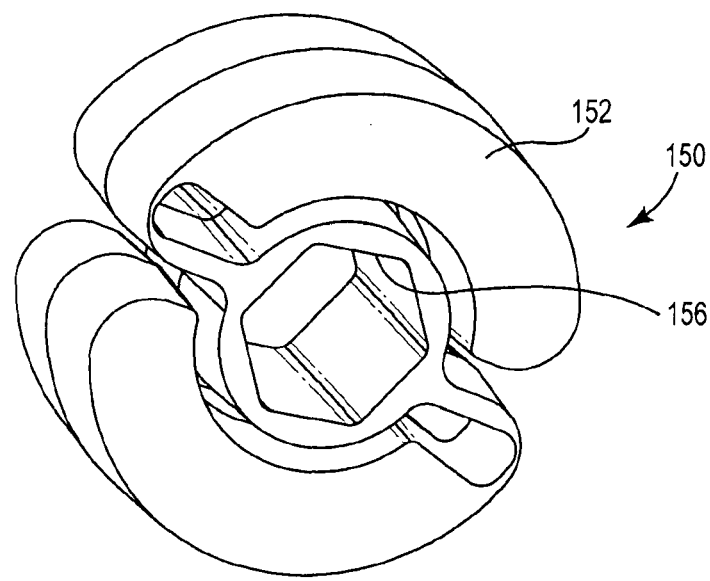
FIG. 37 is a perspective view of a centrifugal brake device for use with a dampening handle device.
Figure 38:
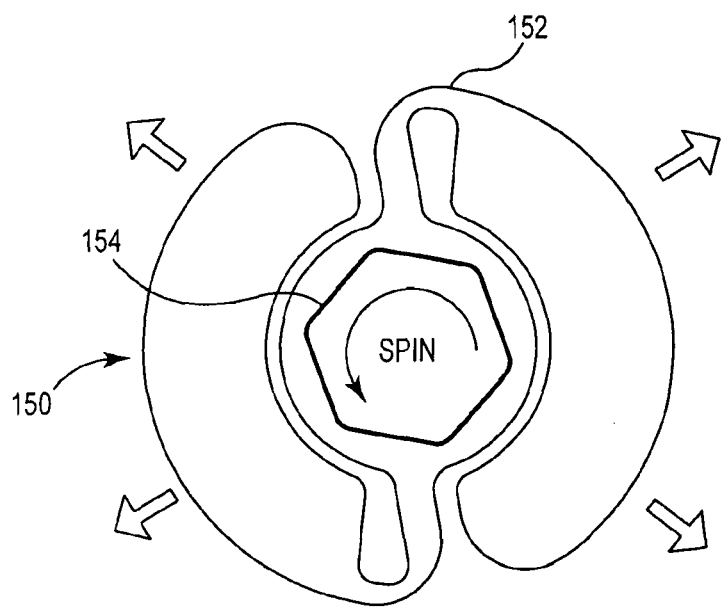
FIG. 38 is a front view of the centrifugal brake device of FIG. 37.

In one embodiment, a centrifugal brake system 150 is provided with the handle device 100, as shown in FIGS. 37-38. The brake system 150 can include a pawl portion 152. In one embodiment, the pawl portion 152 is constructed of an injection molded, low durometer, Pebax™ (polyether block amide), or other acceptable materials known to one skilled in the art. Portion 152 can assume a myriad of shapes and configurations to facilitate the centrifugal braking described herein. Portion 152 includes an inner bore 156 taking on a predefined shape, e.g., hexagonal. A hex feature or member 154 can be provided within the bore 156 such that it is generally permitted to spin within the bore 156, at least for an initial period of time. Upon spinning movement of the member 154 in a counter-clockwise direction, the pawl feature expands outward and initiates friction against the inner diameter of the bore or tube it is disposed within, or a handle portion it is in operative communication with. This frictional engagement of the portion 152 provides desired dampening and braking of the respective handle motion. The system 150 and its components can be disposed within any portion of the handle 100 generally adapted for such a system to dampen handle vibration or "jumping."

Figure 39:
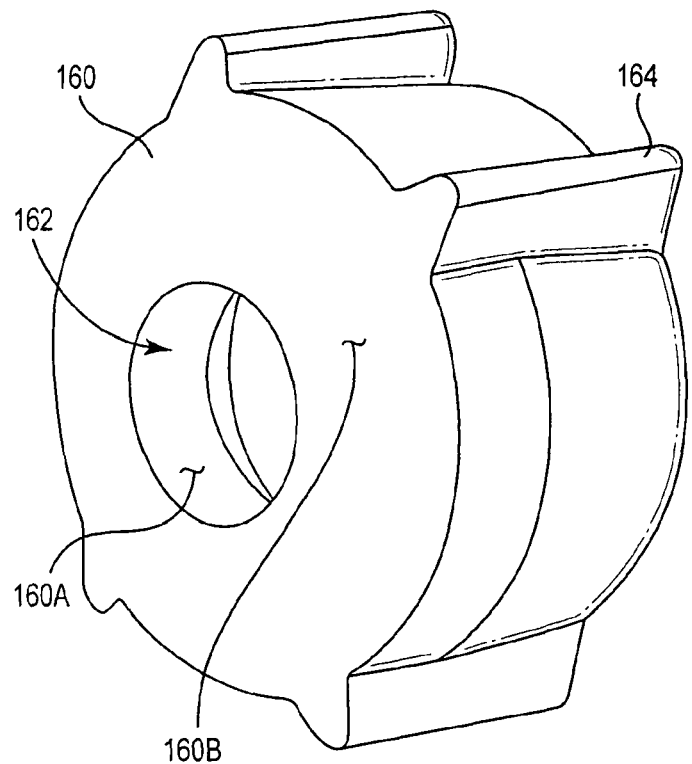
FIG. 39 is a perspective view of a press-in damper device for use with a dampening handle device.
Figure 40:
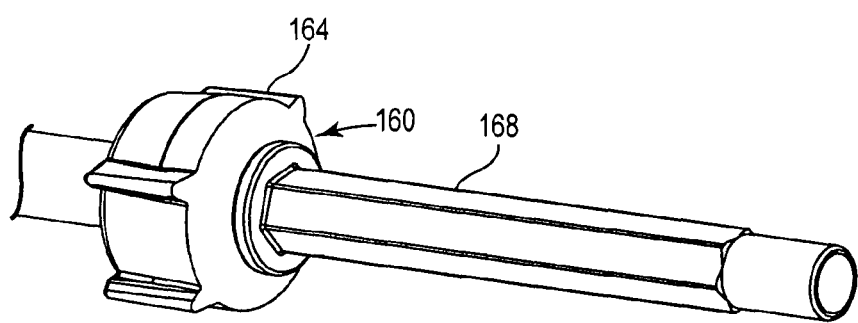
FIG. 40 is a partial perspective view of a handle device having a press-in damper device.

In one embodiment, a press-in damper 160 is provided with the handle device 100, as shown in FIGS. 39-40. The damper 160 can be constructed of an elastomer material, e.g., Santoprene™, TPE (thermo plastic elastomer), and the like. The damper 160 includes an engagement bore 162 and outer mating features 164, with the damper 160 being integrated or otherwise provided with a portion of the main body of the handle 100. The engagement bore 162 is adapted to receive a nut 168 or other component of the handle device 100, with the mating features 164 configured to mate with other components of the handle or catheter delivery system. As such, torquing or other movement of the component 164 provided within the engagement bore 162 provides desired dampening, due at least in part to the friction exerted by and on the elastomer contact surfaces 160A and 160B.

Figure 41:
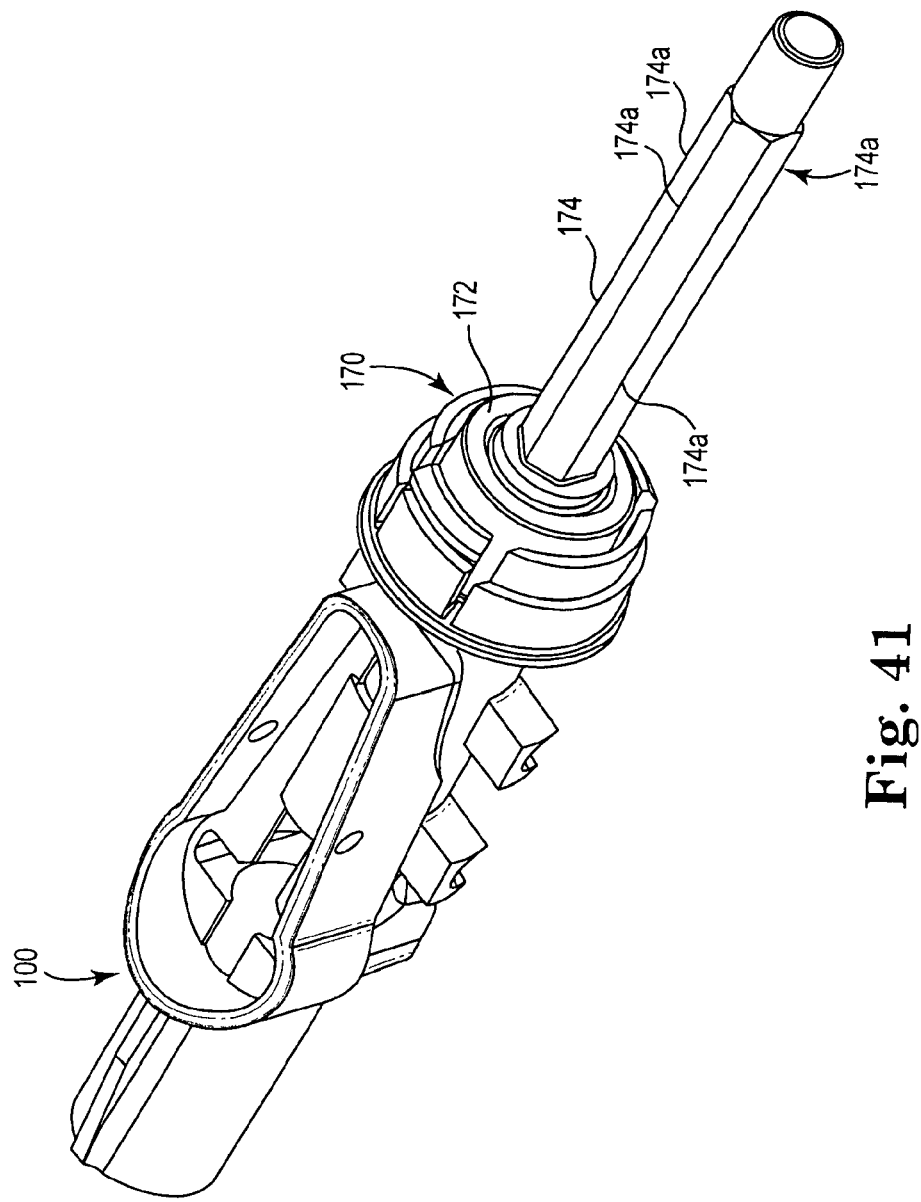
FIG. 41 is a partial perspective view of a handle device having a compression point damper system.
Figure 42:
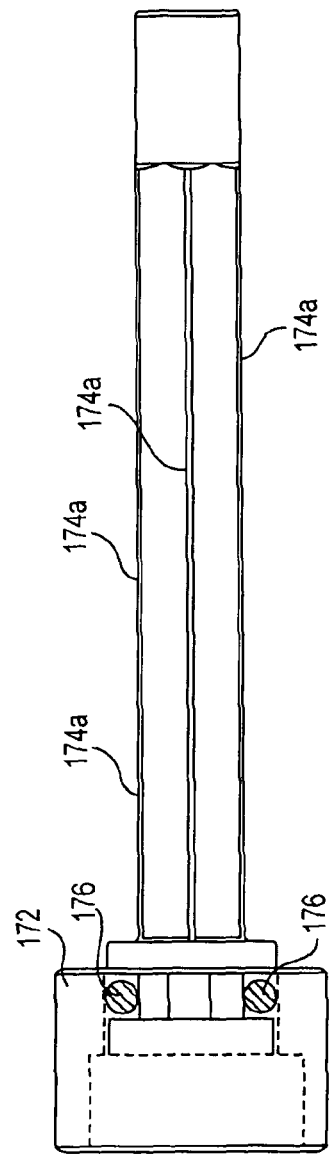
FIG. 42 is a partial cross section view of the compression point damper system of FIG. 41.
Figure 43:
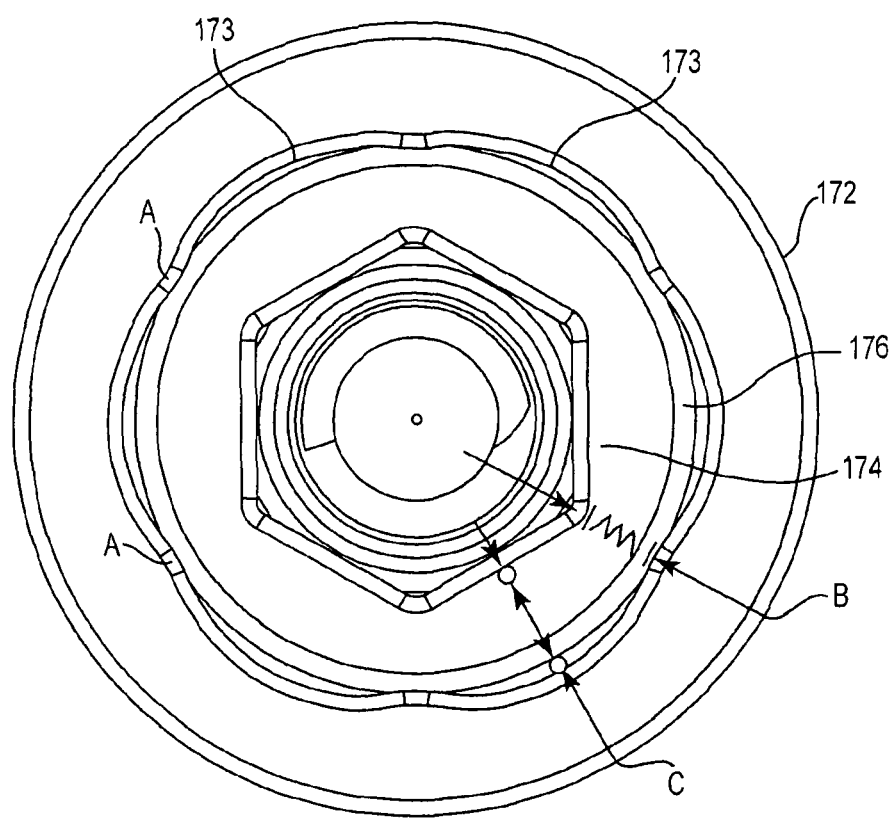
FIG. 43 is a front view of the compression point damper system of FIG. 41.
Figure 44:
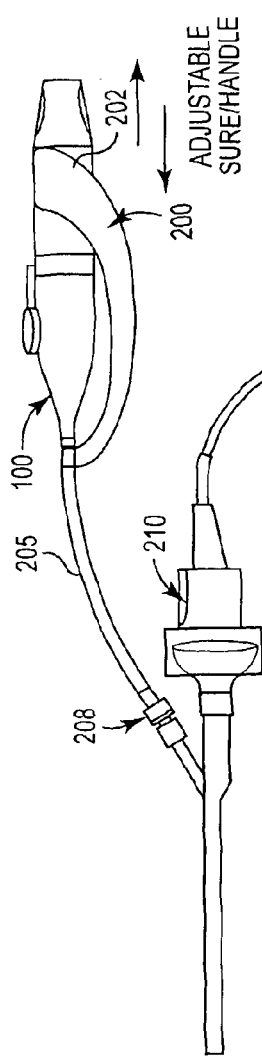
FIG. 44 is a partial perspective view of a hysterscope deployment support device for use with a catheter delivery system and attached to a corresponding handle device.
Figure 45:
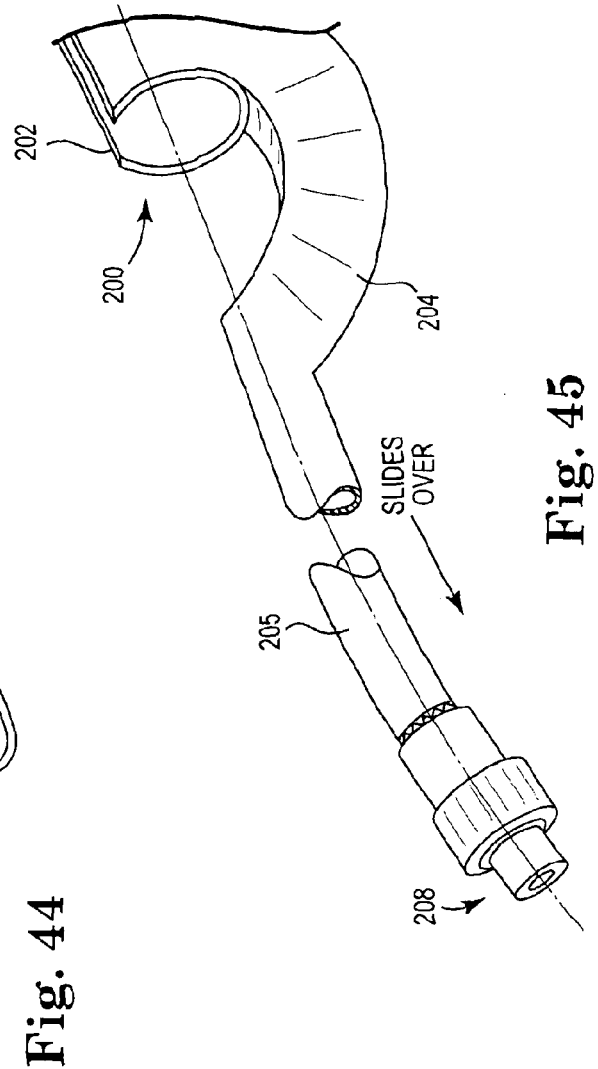
FIG. 45 is a close-up partial perspective view the hysterscope deployment support device of FIG. 44.

In one embodiment, a compression point damper device 170 is provided with the handle device 100, as shown in FIGS. 41-43. The damper device 170 can include a press-in lobed drum 172. The drum 172 can be constructed of various polymers (e.g., ABS) or like materials, and is adapted to integrate or otherwise attach with a portion of the main body of the handle 100. Further, a nut 174 having one or more lobes 174a mates with the drum 172 and its respective internal lobe features 173. As shown in FIG. 42, at least one o-ring 176 is disposed within the drum 172.

As the lobed nut 174 turns or rotates within the drum 172, the o-ring 176 operatively hits a plurality of compression points at least partially created by the configuration of the lobed nut 174. This, in turn, provides segmented friction points that slow the speed of the turning nut 74 and subjects the o-ring 176 to peristaltic motion. The higher the compression ratio, the slower the turning speed of the nut. FIG. 43 shows the various compression points. For instance, compression points A of the lobe features 173 of the drum 172 are shown. Further, the compressed section B of the o-ring 176 is depicted, as well as the clearance C between the o-ring 176 and the mating features. The material and design of the drum 172 and nut 174 components provide advantageous dampening of "jumping" or torquing at the handle 100 during use.

Another embodiment of the handle 100 can include a hysterscope deployment support device 200, as shown in FIGS. 44-47. The support device 200 enables using the handle and catheter delivery system with a hysterscope or other like scope system. Namely, device 200 supports and engages with the handle 100, permitting the device 200 to slide forward and rearward along a portion of the handle 100, and to twist or rotate around the handle 100. This, in turn, frees up the hands of the physician during a procedure because he or she is not required to separately secure or grab each of the devices 100, 200.

The support device 200 includes a clipping portion 202, a spanning portion 204, and a tube portion 205. The clipping portion 202 is sized and configured to clip onto or otherwise engage the handle 100 such that it is capable of the forward, rearward and spinning motion described and depicted herein. The spanning portion 204 generally extends (e.g., arcuate in one embodiment) from the clipping portion 202 to the tube portion 205 and can facilitate holding and handling of the device 200 and the attached handle 100. The tube portion 205 can provide tactile feel for the operatively engaged catheter. In one embodiment, the tube portion 205 can telescope to various lengths. A distal connection portion 208 of the tube 205 can be adapted for engagement with conventional luer lock connections. As shown if FIG. 44, the connection portion 208 can connect with the luer lock of a hysterscopic interface, providing a convenient and quick-connecting interface between the hysterscope camera head 210, the handle 100 and the corresponding catheter delivery system.

Figure 46:
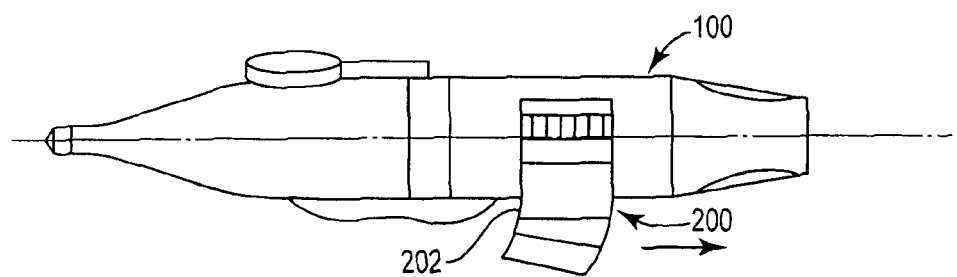
FIG. 46 is a partial side view of a hysterscope deployment support device attached to a handle device.
Figure 47:
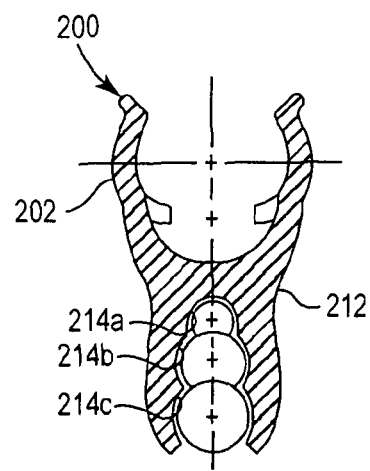
FIG. 47 is a partial cross section view of a hysterscope deployment support device having a plurality of cable receiving portions.

In another embodiment of the support device 200, the clipping portion 202 can extend down to include a cable receiving portion 212, as shown in FIGS. 46-47. The cable receiving portion 212 can include one or more channels 214. The channels 214 can be shaped and sized to accommodate or receive cables (e.g., camera cables) of various diameters. FIG. 47 shows a cable receiving portion 212 having three channels 214a-214c of a predefined shape and size. However, a myriad of sizes, shapes and configurations are envisioned for the channels 214 depending on the particular visualization and scoping requirements for the device.

FIGS. 48-56 show various embodiments of a catheter end portion or tip 250 for use with a delivery system 10 for delivering and deploying a generally proximate occluding member or implant 20. Each of the depicted embodiments is designed to provide a tissue denuding feature to promote tissue disruption and, thus, in-growth at the occluding member 20. For instance, the catheter tip 250 can provide tissue denution or disruption prior to or after deployment of the occluding member 20.

Figure 48:
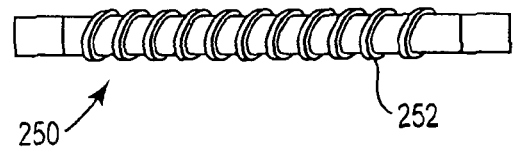
FIGS. 48-56 depict embodiments of a denuding catheter tip for use with the catheter delivery system of the present invention.

FIG. 48 depicts an embodiment of the catheter tip 250 including a wrapped coil element 252. The coil 252 can be tightly wound around the catheter tip and can be constructed of stainless steel or other like materials.

Figure 49:
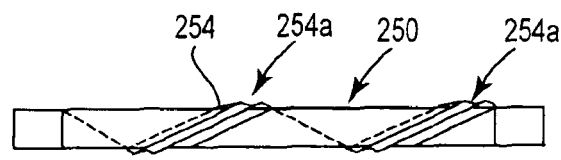

FIG. 49 depicts an embodiment of the catheter tip 250 including a wrapped helix element 254. The helix 254 can include recessed grooves 254a at the peak of the thread. The helix 254 can be high pitched and tightly wound around the tip 250, and can be constructed of Pebax™ or other like materials.

Figure 50:
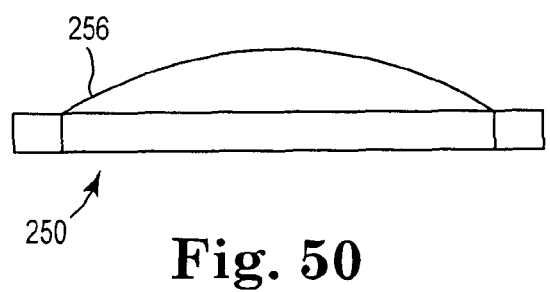

FIG. 50 depicts an embodiment of the catheter tip 250 including a length of rounded wire 256 extending up a distance from the tip 250. The rounded wire 256 can be constructed of Nitinol or other like materials.

Figure 51:
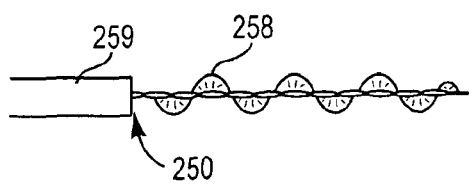

FIG. 51 depicts an embodiment of the catheter tip 250 including a wire brush element 258. The inclined wire brush 258 can be constructed of PET or other like materials. In one embodiment, the outer diameter of the brush 258 is approximately 0.060 inches. A catheter sheath 259 is also shown in FIG. 51. Such a catheter sheath 259 can be included with any of the catheter tip embodiments described or depicted herein.

Figure 52:
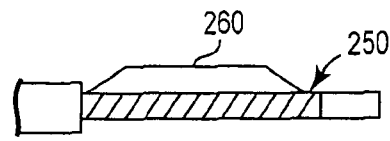

FIG. 52 depicts an embodiment of the catheter tip 250 including a flat ribbon element 260 extending up a distance from the tip 250. The ribbon 260 can be constructed of a relatively flat material, e.g., stainless steel.

Figure 53:
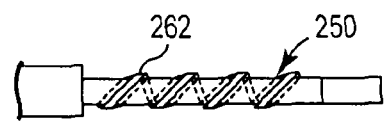

FIG. 53 depicts an embodiment of the catheter tip 250 including a thread ribbon element 262. The ribbon 262 is wrapped around the tip 250 and can be constructed of over-exposed Pebax™ or like materials. The turning points or peaks of the ribbon 262 can, therefore, include a flat point or surface.

Figure 54:

FIG. 54 depicts an embodiment of the catheter tip 250 including a metal ribbon element 264. The ribbon 264 can be constructed of Nitinol or like materials, with a flat top surface created by over-expanding the ribbon. The ribbon 264 is generally loosely wound around the tip 250.

Figure 55:
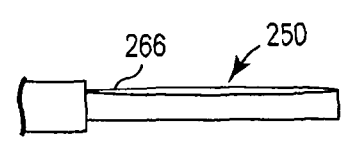
Figure 56:
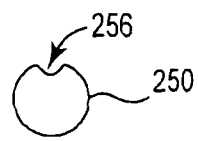

FIGS. 55-56 depicts an embodiment of the catheter tip 250 including a grooved element 266. In one embodiment, the grooved element 266 is formed by melting a groove (e.g., round groove) along a portion of the element 266 or tip 250 made of Pebax™ or like materials. FIG. 56 shows a front view of the tip 250 and corresponding groove.

Figure 57:
FIG. 57 is a side view of a wire denuding brush.

FIG. 57 depicts a brush member 280 adapted for use in conjunction with a catheter delivery system of the present invention. The brush member 280 can be constructed of a large wire and/or wire brush material and is generally stiff. As such, the brush member 280 can be used to denude tissue within the body lumen 34 and removed prior to introduction of the catheter or occluding member 20.

All patents and publications referenced herein are hereby incorporated by reference in their entireties.

It will be understood that certain of the described structures, functions and operations of the above-described preferred embodiments are not necessary to practice the present invention and are included in the description simply for completeness of an exemplary embodiment or embodiments. It will also be understood that there may be other known structures, functions and operations ancillary to the typical surgical procedures that are not disclosed, but that can be implemented to practice the present invention. It is, therefore, to be understood that within the scope of the appended claims, the invention may be practiced other than as specifically described without actually departing from the spirit and scope of the present invention.

What is claimed is:

1. A catheter delivery system for deploying an occluding device in a body lumen, comprising:
    a catheter;
    an occluding device provided at a distal portion of the catheter, the occluding device configured for deployment within the body lumen;
    a handle device operatively coupled with the catheter, the handle device including;
        an actuator;
        a rotatable interface member to operatively couple the handle device with the catheter; and
        a damper device operatively coupled with the rotatable interface member to reduce the vibration on the handle device from deployment of the occluding device upon rotation of the rotatable interface member within the damper device.

2. The delivery system of claim 1, wherein the rotatable interface member comprises a hex feature, and the damper device includes a centrifugal brake element adapted to operatively engage the hex feature such that the centrifugal brake element generally expands outward upon rotation of the hex feature.

3. The delivery system of claim 1, wherein the rotatable interface member comprises a hex feature, and the damper device includes a press fit elastomer element adapted to operatively engage the hex feature such that one or more surfaces of the press fit elastomer element exert a friction force against the hex feature upon rotation of the hex feature.

4. The delivery system of claim 1, wherein the rotatable interface member comprises a hex feature, and the damper device includes a lobed drum device adapted to operatively engage with the hex feature to define a plurality of compression points to slow rotation of the hex feature.

5. The delivery system of claim 1, wherein the occluding device includes a gel provided along one or more portions of the occluding device to facilitate occlusion of the body lumen.

6. The delivery system of claim 1, wherein the occluding device includes an open lattice structure.

7. The delivery system of claim 1, wherein the catheter includes a tip portion having one or more denuding features adapted to disrupt tissue within the wall of the body lumen to facilitate tissue in-growth at the occluding device.

8. The delivery system of claim 1, further comprising a transurethral delivery device proximate the occluding device to locally inject or spray a scarring agent within the body lumen.

9. The delivery system of claim 1, wherein the damper device includes a centrifugal brake element adapted to operatively engage the rotatable interface member such that the centrifugal brake element generally expands outward upon rotation of the rotatable interface member within the damper device.

10. The delivery system of claim 1, wherein the damper device includes a press fit elastomer element adapted to operatively engage the rotatable interface member such that one or more surfaces of the press fit elastomer element exert a friction force against the rotatable interface member upon rotation of the rotatable interface member within the damper device.

11. The delivery system of claim 1, wherein the damper device includes a lobed drum device adapted to operatively engage with the rotatable interface member to define a plurality of compression points to slow rotation of the rotatable interface member within the damper device.

12. A method of deploying an occluding device in a body lumen, comprising:
inserting a catheter into a body lumen, wherein a handle device is operative coupled with the catheter, and the handle device includes a rotatable interface member operatively coupled with the catheter and a damper device operatively coupled with the rotatable interface member;
deploying an occluding device from the catheter within the body lumen, wherein deploying comprises rotating the rotatable interface member within the damper device such that the damper device reduces vibration on the handle device from deployment of the occluding device from the catheter.

13. The method of claim 12, wherein the catheter includes a tip portion having one or more denuding features adapted to disrupt tissue within a wall of the body lumen to facilitate tissue in-growth at the occluding device.

14. The method of claim 12, wherein the occluding device includes a lattice structure.

15. The method of claim 12, wherein the rotatable interface member comprises a hex feature.

16. The method of claim 15, wherein rotating the rotatable interface member such that the damper device reduces vibration on the handle device from deployment of the occluding device from the catheter comprises:
expanding a centrifugal brake element outward upon rotation of the hex feature, wherein the centrifugal brake element is operatively engaged with the hex feature.

17. The method of claim 15, wherein rotating the rotatable interface member such that the damper device reduces vibration on the handle device from deployment of the occluding device from the catheter comprises:
exerting a friction force against the hex feature upon rotation of the hex feature with one or more surfaces of a press fit elastomer element operative engaged with the hex feature.

18. The method of claim 15, wherein rotating the rotatable interface member such that the damper device reduces vibration on the handle device from deployment of the occluding device from the catheter comprises:
exerting a plurality of friction points on a lobed drum device operative engaged with the hex feature upon rotation of the hex feature.

\* \* \* \* \*